United States Patent [19]

Gondouin

[11] Patent Number: 4,705,908
[45] Date of Patent: Nov. 10, 1987

[54] NATURAL GAS CONVERSION PROCESS

[76] Inventor: Oliver M. Gondouin, c/o S Cal Research Corp., 32 San Marino Dr., San Rafael, Calif. 94901

[21] Appl. No.: 688,058

[22] Filed: Dec. 31, 1984

[51] Int. Cl.$^4$ .............................................. C07C 2/00
[52] U.S. Cl. ................................... 585/500; 585/300; 585/415; 585/417; 585/541; 585/661; 585/943
[58] Field of Search ............... 585/300, 500, 415, 943, 585/417, 661, 541

[56] References Cited

U.S. PATENT DOCUMENTS

| | | | |
|---|---|---|---|
| 4,100,218 | 7/1978 | Chen et al. | 585/330 |
| 4,199,533 | 4/1980 | Benson | 585/500 |
| 4,205,194 | 5/1980 | Mitchell et al. | 585/500 |
| 4,350,835 | 9/1982 | Chester et al. | 585/415 |
| 4,443,647 | 4/1984 | Jones et al. | 585/417 |
| 4,450,310 | 5/1984 | Fox et al. | 585/500 |
| 4,465,893 | 8/1984 | Olah | 585/500 |
| 4,507,517 | 3/1985 | Devries et al. | 585/943 |

OTHER PUBLICATIONS

Fang et al, *J. Chinese Chem. Soc.*, 29, pp. 265–273, 1981.

Primary Examiner—Curtis R. Davis

[57] ABSTRACT

Natural gas hydrocarbon components, methane to butanes, are converted into low-vapor-pressure liquid hydrocarbons in a combination process which comprises successively passing the heavier fraction ($C_2$ to $C_4$) and the lighter fraction ($C_1$, $C_2$) with hydrogen over a non silica-based catalyst including crystals of basic mixed oxides and recovering $C_5+$ hydrocarbons. First the heavier fraction of the feed ($C_2+$) is converted at temperature below 600° C. over a fluidized or moving catalytic bed. Condensible $C_3+$ products are fractionated for $C_5+$ recovery and for $C_3$, $C_4$ recycling. Gas by-products $H_2$, $C_1$, $C_2$, are separated into an enriched hydrogen stream and into a $C_1$, $C_2$ by-product gas which is recycled into the lighter fraction $C_1$, $C_2$ of the feed. The resulting lean gas mixture is then reacted with an ionized hydrogen plasma derived from the enriched hydrogen stream, in the presence of the same catalyst in a short residence time reactor. The catalyst, introduced in this reactor at a temperature below 600° C. is also used as a heat transfer medium to quench the reaction. The condensible product in the gaseous effluent from the short residence time reactor is recovered and the gaseous by-products are recycled to the separation unit for hydrogen extraction. The process is of particular interest where natural gas has a relatively low market value.

17 Claims, 8 Drawing Figures

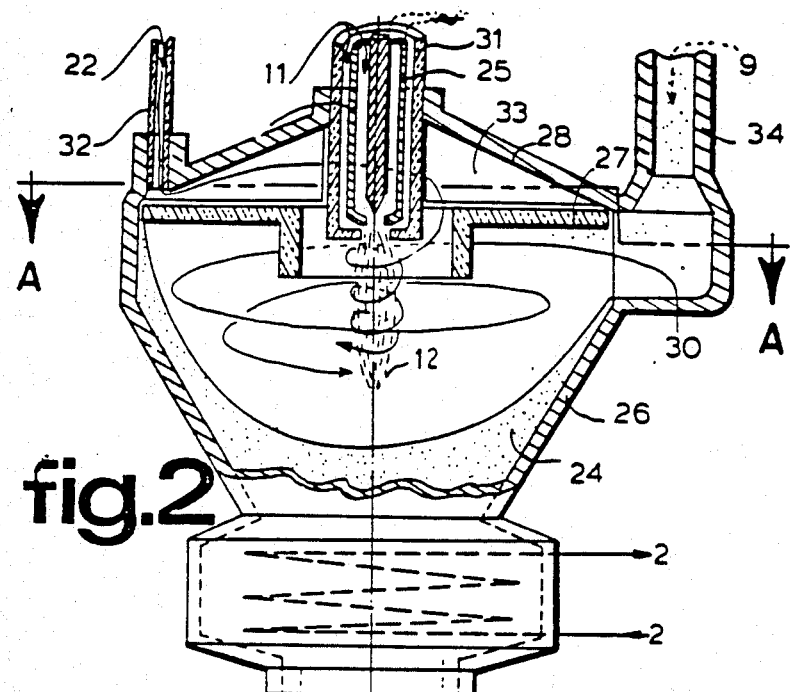
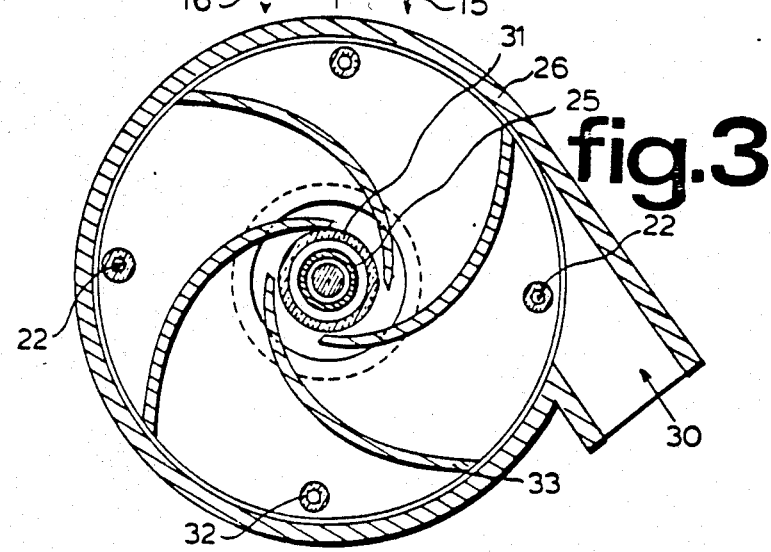

NATURAL GAS CONVERSION PROCESS

BACKGROUND OF THE INVENTION

1. Field of the Invention

The present invention is concerned with an improved process for converting natural gas into a low-vapor-pressure liquid hydrocarbon mixture, which for instance can be more easily transported from a remote oil or gas field to a market. More particularly, this invention deals with a novel processing scheme to convert light gases (Methane to Butanes) into aromatics, $C_5+$ hydrocarbons and a hydrogen-rich by-product gas. This process, if applied in a petroleum refinery, also allows to increase the yield of higher value liquid products (BTX) at the expense of less valuable gas products. This process may also be used to produce hydrogen from natural gas.

2. Description of Prior Art

Conversion of the $C_1$-$C_4$ fractions of Natural Gas into higher molecular weight components is commonly achieved by first fractionating the feed into essentially pure components, such as Ethane or Propane and then converting each fraction individually into heavier, more valuable components such as olefins or aromatics, using either non catalytic thermal processes (e.g. steam pyrolysis or thermal cracking for the conversion of Ethane into Ethylene), or catalytic dehydrogenation processes or a combination of both types of processes in which an essentially pure lighter feed component, Ethane for example, is first converted into Ethylene by steam cracking at high temperature, and the Ethylene is separated and subsequently converted to aromatics catalytically at moderate temperature in a second step. The catalysts used are composed primarily of Silica ($SiO_2$) in the form of Silicates or Alumino-Silicates. It is claimed that the acidic nature of the Silica-based catalysts (Bronsted acid sites) or the cage-like structure of the catalyst crystal (such as a ZSM-5 zeolite) are determining factors in these conversion processes. Some of these processes are oxidative in nature and result in the formation of oxidation products, such as water, which have no fuel value and must be separated from the hydrocarbon product. Still, other processes use "super acids" as catalysts, including various oxidative reagents (Fluorine, Chlorine, Sulfates . . . ). These processes also result into oxidation products which must be separated out for disposal or for reclaiming.

Some of the known catalytic processes for the conversion of lighter components $C_1$, $C_2$, of natural gas, mostly produce light olefins and LPG components which must then be separated out and converted to heavier components in a second step, using different catalysts.

The early commercial processes (Fischer-Tropsch) available to produce hydrocarbon liquids from gases did not use natural gas as a feed stock but various mixtures of CO and $H_2$. These can be derived from natural gas by various oxidative processes, so that the conversion of natural gas into hydrocarbon liquids requires additional preprocessing and the use of several different catalysts. These processes based on Syngas ($CO+2H_2$) also proceed through many intermediate steps in which oxygenated products (Methanol for instance) are formed and must be separated, purified and de-oxygenated into other intermediate chemical specie before reaching the final goal of a marketable liquid hydrocarbon mixture. The catalysts used in these processes generally contain large amounts of Silica. Thermal pyrolysis of Methane in an electric arc furnace has been used to produce acetylene, which is a much more stable component at very high temperatures than aromatics or naphta, in the absence of any catalyst. Although acetylene is an important raw material for organic synthesis, it is not easily transportable, and cannot be marketed together with crude oil or condensate as a liquid mixture.

SUMMARY OF THE INVENTION

The present invention combines the use of a single catalyst over a wide range of temperatures to convert successively 1° a mixture of the heavier components of the natural gas (principally the available Propane and Butanes with a portion of the available Ethane) at moderate temperatures and relatively long residence times, in a catalytic bed reactor, and 2° a mixture of light gas components $C_1$, $C_2$, and $H_2$ at high temperature and very short residence times in a cyclone reactor. The conversion order may also be reversed. The first step of the process is therefore to split the feed gas into a Rich Gas stream ($C_2$, $C_3$, $C_4$), and a Lean Gas stream ($C_1$, $C_2$); this is accomplished in a Feed Splitter unit of conventional design. The catalyst used for this dual conversion process is handled as a fluidized or moving bed which, for the Rich Gas conversion, may be subject either to an upward flow in a reactor similar to a fluid catalytic cracking (FCC) reactor, or to a gravity-assisted flow in a moving bed reactor similar to CCR or TCC reactors For the conversion of Lean Gas ($C_1$, $C_2$), the catalyst flowing respectively to the top or bottom of the catalytic bed reactor in these two cases, when the Rich Gas conversion occurs first, reaches an overflow standpipe of conventional design leading into the cyclone reactor, through an inlet located at the periphery of the cylindrical cavity of the cyclone. The catalyst particles, falling into the cyclone reactor meet the tangential flow of the pre-heated Lean Gas feed into the cyclone. This gas flow carries the catalyst in a downward spiral motion against the conical surface of the cyclone reactor, and from there it is led into a disengagement cyclone which may also be combined with the cyclone reactor.

The reaction products are separated from the spent catalyst in the disengagement cyclone and in a conventional steam stripper. In the cyclone reactor a cold enriched hydrogen stream is fed through an axial insulated pipe into the reactor, where it is subjected to intense heat by electricity or other known means (for instance a high frequency electromagnetic field combined with a starter electric arc). As a result, the hydrogen is dissociated into an ionized plasma confined to a central region located along the vertical axis of the cyclone reactor.

The Lean Gas feed stream to the cyclone reactor, containing primarily $C_1$ and $C_2$ hydrocarbons together with residual $H_2$ from recycle streams and minor quantities of $C_3$ and non hydrocarbon impurities, is pre-heated in a conventional furnace to a temperature of 700° C. to 1000° C. (but not exceeding the feed's incipient pyrolysis temperature). It is then injected tangentially into the cylindrical cavity of the cyclone reactor.

The catalyst fed into the cyclone reactor is at a temperature significantly lower, less than 600° C. Despite the high temperature of the feed gas, the peripheral wall temperature of the cyclone remains well below 900° C.

The temperature of the catalyst itself also does not exceed 900° C. when it comes out of the cyclone part of the reactor, but the refractory properties of the oxide components of the catalyst allow it to withstand the thermal shock resulting from local short term exposure to the very high temperature central region of the reactor without degradation of the crystalline structure of the catalyst. Further cooling of the catalyst and of the reaction products occurs in the heat recovery section of the reactor below the conical cavity of the cyclone. The Rich Gas stream is the cooling medium.

The chemical composition of the dehydrogenation catalyst is characterized by the following formula:

$$xMO_2, yM'M''O_3, zM'''O_2$$

where
- x, y and z are mole fractions ranging from 0 to 98 percent, and x is greater than y, which is greater than z,
- M is an Actinide tetravalent metal, such as Thorium,
- M' is a trivalent metal such as Gallium,
- M'' is a Lanthanide trivalent metal, such as Lanthanum,
- M''' is a tetravalent metal, such as Zirconium or Hafnium, The catalyst can tolerate small amounts of hydrogen sulfide and of Sulfur components without being poisoned. It can also tolerate the presence in the Natural Gas feed of significant percentages of carbon dioxide, especially if the carbon dioxide fraction is in majority directed to the Rich Gas stream from the feed splitter unit.

The injection of relatively cold catalyst into the cyclone reactor quenches the dehydrogenation reactions and provides an effective screen against heat radiation from the central plasma region towards the cylindrical and conical walls of the cyclone reactor. The high velocity spiral flow of catalyst particles suspended in the gas phase facilitates the transfer of heat towards the outside, through the reactor wall.

Heat radiation towards the top of the reactor is reduced by the use of a heat shield made of known refractory materials (ceramics, carbides, tungsten foil, graphite, etc . . . ). Further cooling of the top wall of the reactor is achieved by the injection of a secondary cold hydrogen-rich stream into inlets located at the periphery of the top wall. The cooling gas flows above the heat shield in spiral or helicoidal channels along guiding vanes below the top wall of the reactor, and exits into the cylindrical cavity near the center of the reactor, through openings in the heat shield. The spiraling secondary hydrogen stream, heated by contact with the back face of the heat shield then flows downward in a swirling motion around the plasma jet, and exits through the reactor outlet either unseparated from the spent catalyst or mixed with the separated gaseous phase containing the reaction products. Along this path many molecules of the secondary hydrogen stream become ionized by the plasma. The hydrogen ions collide with gas molecules contained in the tangential inlet feed stream which, by design, rotates in the opposite direction of the secondary hydrogen stream. The increased number of collisions of relatively low energy hydrogen ions with hydrocarbon molecules and with free radicals enhances the yield of the dehydrogenation reactions.

Although the catalyst inhibits the formation of carbon, it eventually becomes loaded with coke, with a corresponding reduction in effectiveness. Regeneration of the catalyst is achieved in a conventional manner by burning the coke in a fluidized or moving bed regenerator at temperatures not exceeding 600° C. The regenerated catalyst is maintained in an oxygen-free atmosphere until it is recycled into the catalytic bed reactor for conversion of additional $C_3C_4$ from the Rich Gas feed.

The spent catalyst coming out of the cyclone reactor and separated from the gaseous effluent of the reactor in the disengagement cyclone contains not only coke, but also some of the heavy hydrocarbon components generated by the dehydrogenation reactions. These heavy hydrocarbons are stripped off the catalyst with steam in a conventional fluidized bed stripper, preferably located directly below the disengagement cyclone, so that the stripped hydrocarbons and steam may be entrained by the gaseous effluent from the disengagement cyclone. Such an arrangement is well known from those skilled in the art.

The hydrogen required for the primary and secondary hydrogen streams fed into the cyclone reactor is obtained by separation from the gaseous effluents streams of both the catalytic bed reactor and the cyclone reactor. These two effluents are separated by conventional means into four streams:
- a hydrogen-rich stream
- a lean gas ($H_2$, $C_1$, $C_2$) recycle stream
- a rich gas ($C_2$, $C_3$, $C_4$,) recycle stream
- a product ($C_5+$) stream For economies of scale, the separation unit is preferably the same for both effluent streams and may include for instance:
- a gas chiller to condense the $C_2+$ fraction,
- a low temperature separator (LTS) separating $H_2$, $C_1$, $C_2$ vapor phase,
- a hydrogen extraction unit which may operate by pressure swing adsorption or by membrane separation, cryogenic separation, or any other method known to those skilled in the art.
- a fractionation column to separate the $C_5+$ product from the $C_2$, $C_3$, $C_4$ fraction of the LTS condensed liquid.
- compression means and auxiliary facilities as required for such a conventional process which is well known of those skilled in the art.

Some of the facilities may be common to both the Feed Splitter Unit and to the Separation Unit.

The transfer of catalyst from the regenerator to the catalytic bed reactor is accomplished by conventional means, (transfer lines, riser reactor, lift pot, lift lines, etc. . . . ) well known of those skilled in the art.

In a preferred embodiment of the invention, the cyclone reactor is located within the catalytic bed reactor so that the heat flux through the cyclone reactor wall contributes to heating the catalytic bed reactor. Another source of heat for the catalytic bed reactor is provided by the hot regenerated catalyst resulting from the coke combustion.

BRIEF DESCRIPTION OF THE DRAWINGS

FIG. 2 is a vertical cross section of the cyclone reactor showing the respective disposition of the inlets for the Lean Gas Feed, the catalyst, the primary hydrogen stream, the secondary hydrogen stream. It also shows the respective paths of the secondary hydrogen and of a tangential stream of Lean Gas Feed and catalyst. The high frequency current producing the ionized hydrogen plasma is shown schematically. The heat recovery section is also shown schematically.

FIG. 3 is a horizontal cross section AA of the top of the cyclone reactor, showing the spiral channels used to impart a swirling motion to the secondary hydrogen stream in the opposite direction of that of the Lean Gas Feed and catalyst stream.

Figure 4:
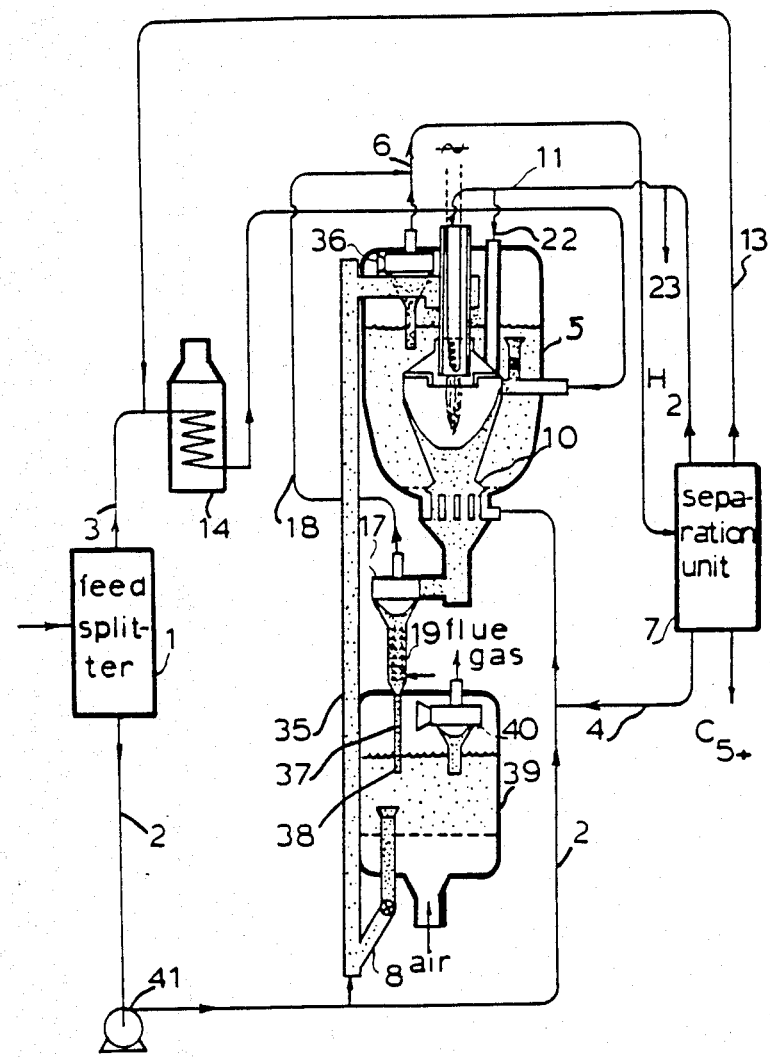

In the embodiment on the flow diagram of FIG. 4, the cyclone reactor is located within a fluidized bed reactor. The transfer of regenerated catalyst back to the fluidized bed reactor is obtained by means of a riser reactor. The Feed Gas splitting unit and the reactor effluent gas separation unit, both of conventional design, are not detailed.

Figure 5:
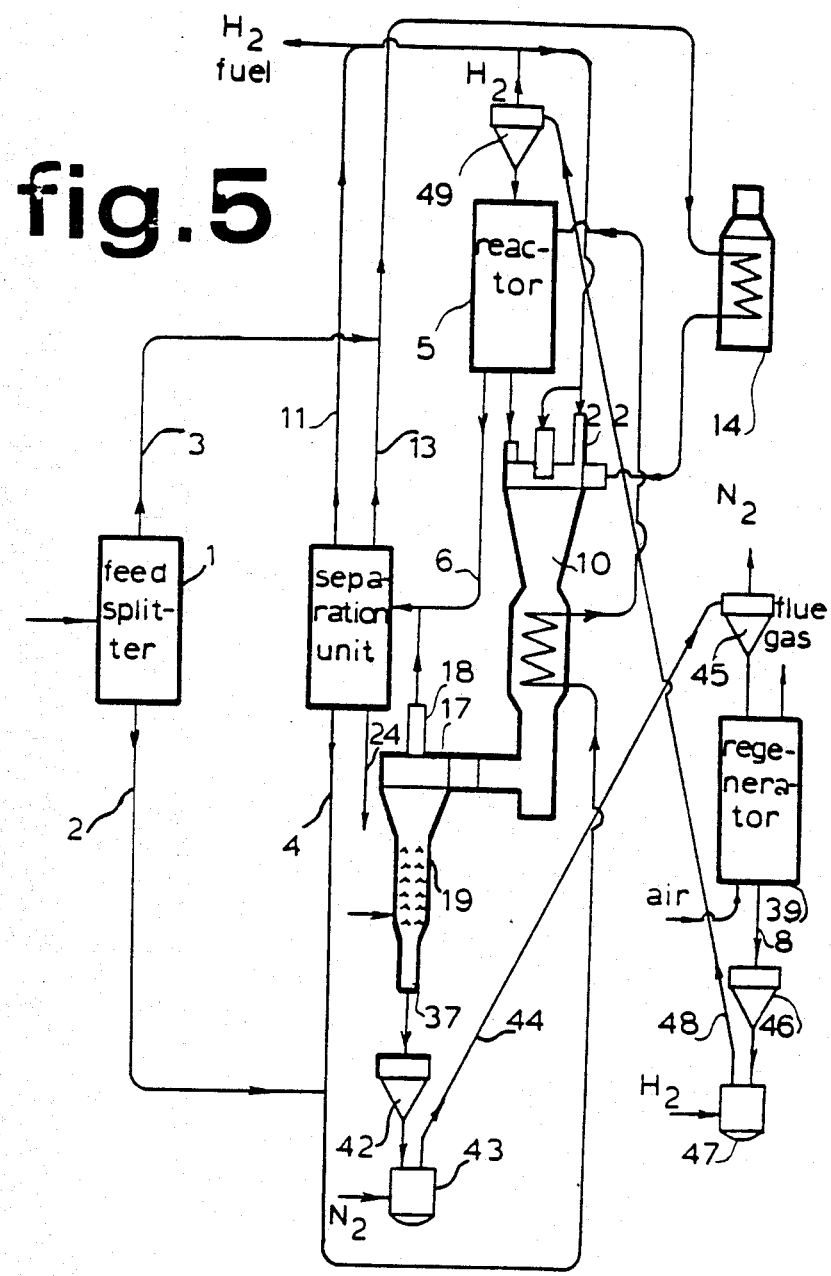

In the embodiment shown on the flow diagram of FIG. 5, the catalytic bed reactor is a moving bed reactor of conventional design, and is not detailed. The transfer of the spent catalyst into the regenerator and of the regenerated catalyst back into the moving bed reactor is obtained by means of lift pots and lift lines of conventional design.

Figure 6:
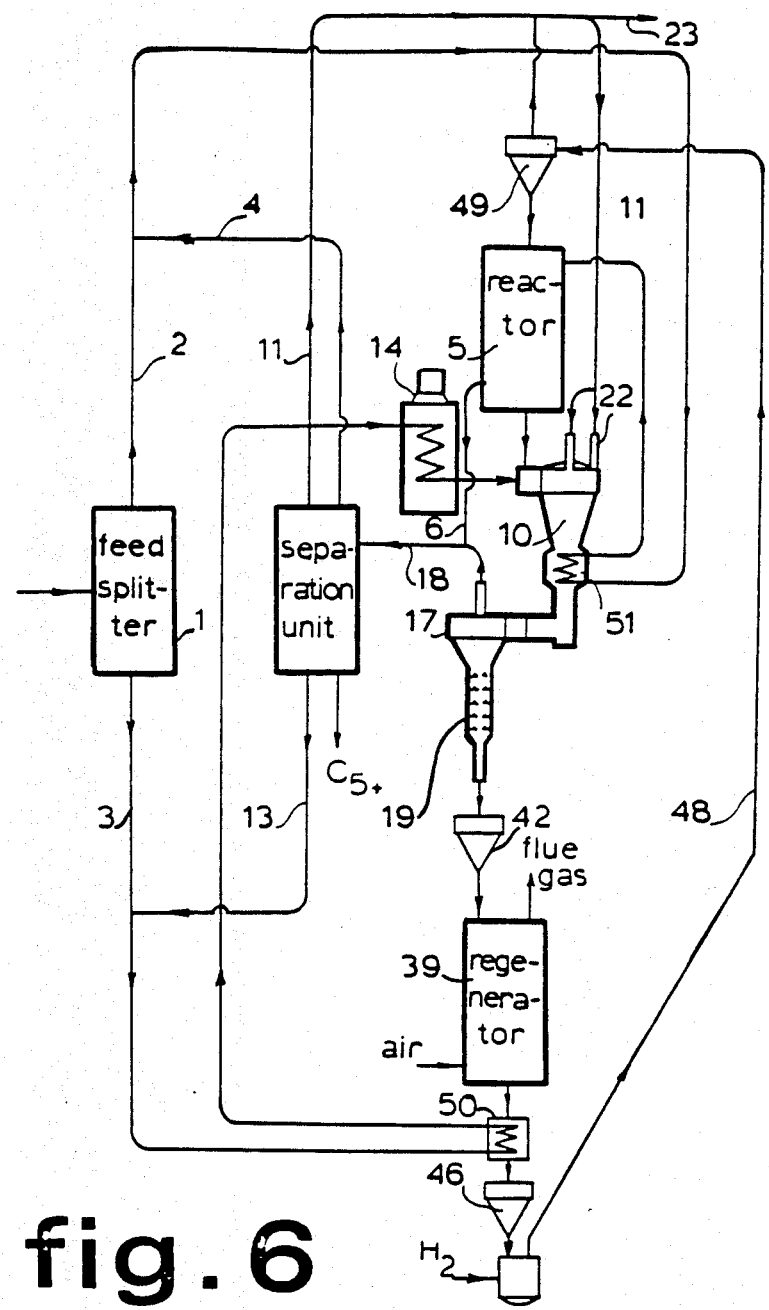

FIG. 6 is a flow diagram of another embodiment of the process in which the catalyst flows by gravity from a moving bed reactor at the top into the cyclone reactor below, and descending from there to the disengagement cyclone, the steam stripper, and finally the moving bed regenerator. The regenerated catalyst is then collected in a lift pot at the bottom and transported upwards by lift gas to a hopper above the moving bed reactor.

The moving bed reactor, moving bed regenerator, and catalyst transport system, all of conventional design, are not detailed.

Figure 7:
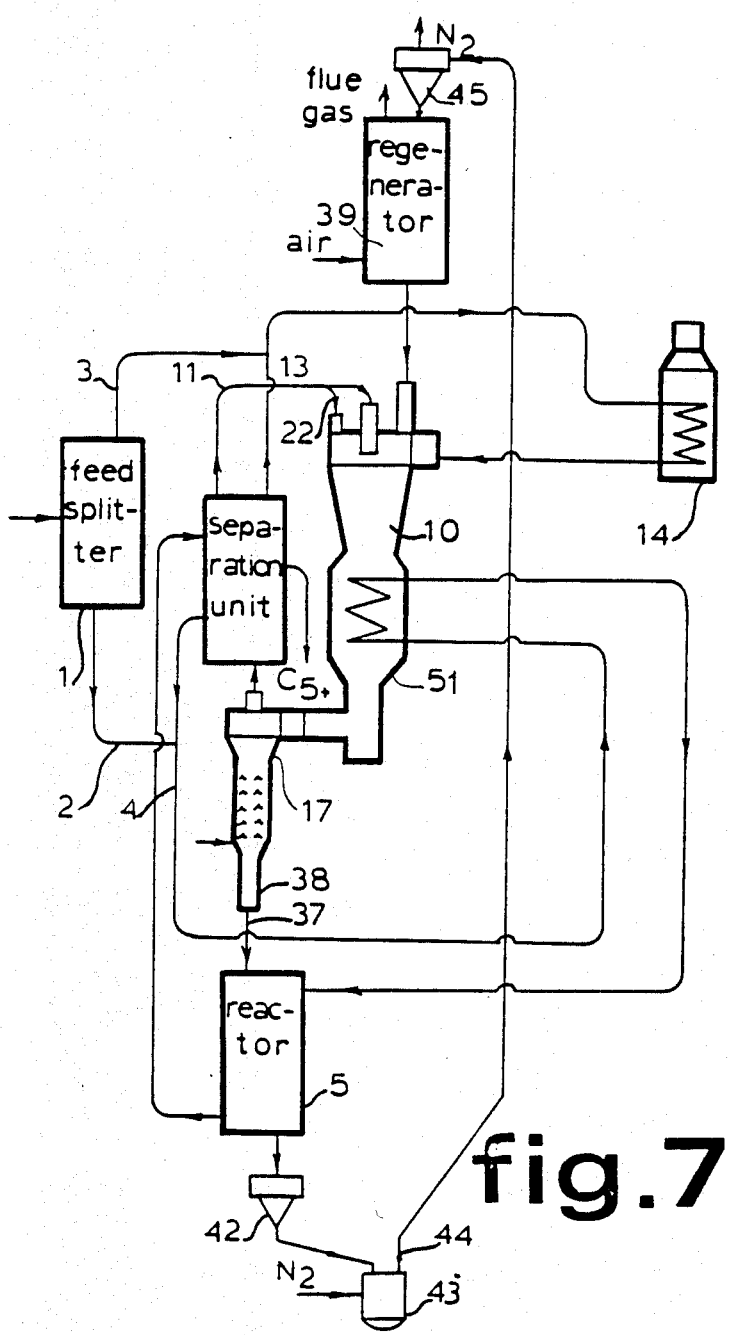

A case in which the Lean Gas conversion occurs first, followed by Rich Gas conversion in a moving bed reactor is shown on FIG. 7. In this variant of the process, the regenerated catalyst is used for Lean Gas conversion and the stripped catalyst is used for Rich Gas conversion.

Figure 8:
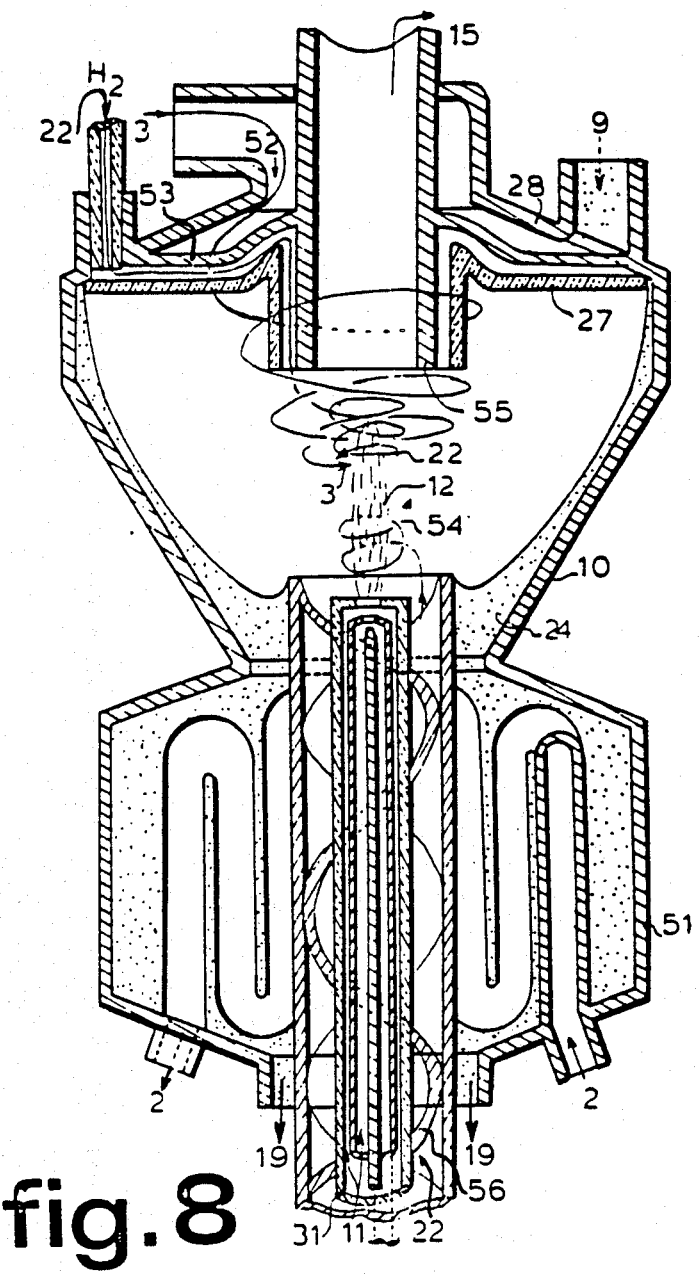

FIG. 8 shows another embodiment wherein the functions of the cyclone reactor and of the disengagement cyclone are combined in a single vessel. The hydrogen plasma jet in this case flows upwards instead of downwards, as in FIG. 2 and FIG. 4. FIG. 8 shows a vertical cross-section of the vessel and internals which combine the functions of cyclone reactor, disengagement cyclone and heat recovery section.

DETAILED DESCRIPTION OF THE INVENTION

Process Description

Figure 1:
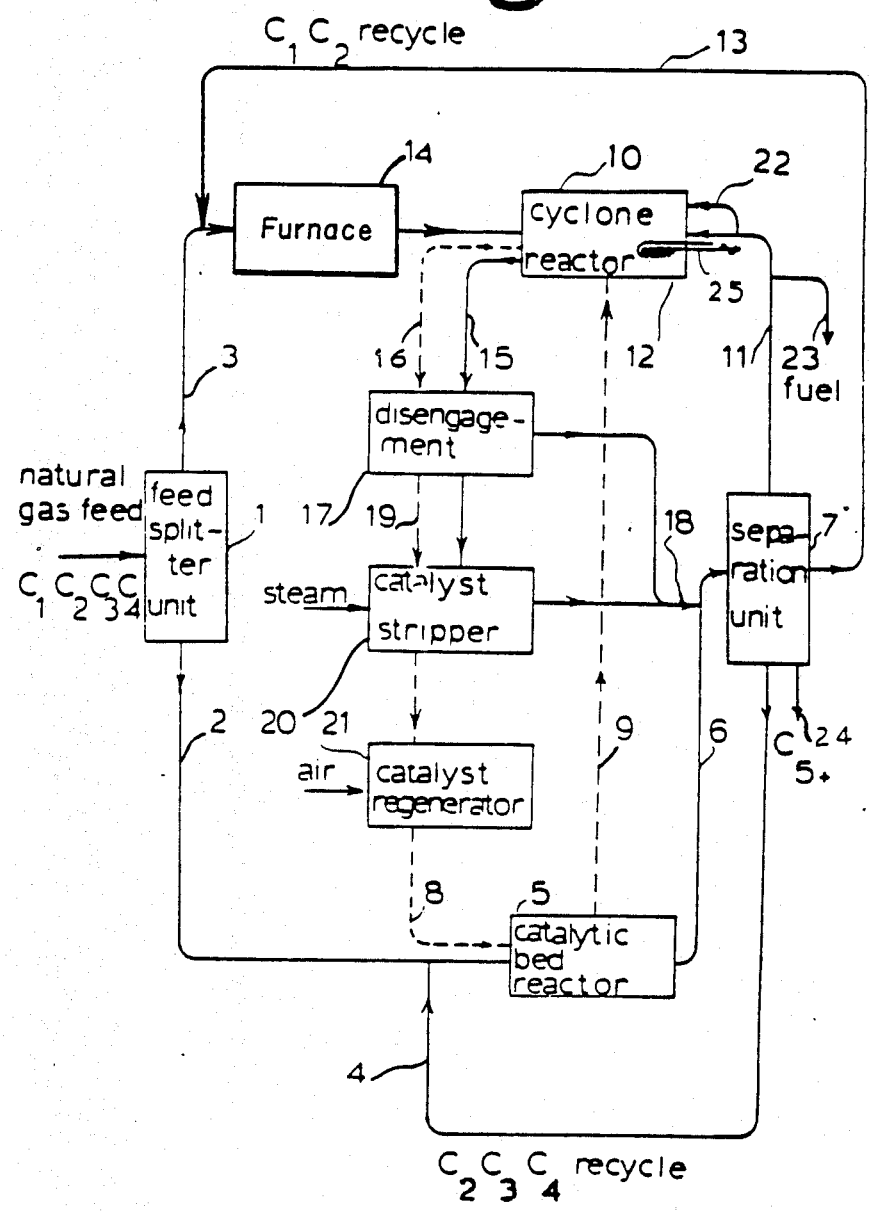
FIG. 1 is a schematic block diagram of the natural gas conversion process, showing the catalyst circulation and the flow of feed, products and recycle streams when Rich Gas conversion occurs first.

Referring to FIG. 1, the following successive steps of the conversion process when Rich Gas conversion occurs first are as follows:

1. In the splitter unit (1) of conventional design, the Natural Gas Feed is split into a Rich Gas Feed (2), and a Lean Gas Feed (3).
2. The Rich Gas Feed (2), together with the $C_2C_3C_4$ recycle stream (4) from the separation unit is fed to the catalytic bed reactor (5).
3. The gaseous effluent (6) from the catalytic bed reactor is fed into the separation unit (7) of conventional design.
4. The regenerated catalyst (8) enters the catalytic bed reactor and exits from it (9), to enter the cyclone reactor (10).
5. The hydrogen stream (11) obtained in the separation unit (7) is injected into the cyclone reactor (10) to produce the ionized hydrogen plasma (12).
6. The Lean Gas stream (3) together with the $C_1C_2$ recycle stream (13) obtained in the separation unit is heated in the furnace (14) prior to injection into the cyclone reactor (10).
7. The gaseous effluent (15) from the cyclone reactor, together with the spent catalyst (16) enter the disengagement cyclone (17).
8. The catalyst effluent (19) from the disengagement cyclone (17) is fed to the catalyst stripper (20) and from there to the catalyst regenerator (21).
9. A portion of the hydrogen stream (11) is used as a secondary hydrogen cooling medium (22) and is fed to the cyclone reactor.
10. The remainder (23) of the hydrogen generated in the separation unit is diverted for use as process fuel or for other applications.
11. The liquid hydrocarbon product (24) obtained from the separation unit is recovered for sale.
12. The block diagram of FIG. 1 shows a coil (25) indicating that the primary hydrogen stream is subjected to a high frequency electromagnetic field in order to produce the ionized plasma.

Preparation of the Catalyst

The catalyst is prepared by co-precipitation of insoluble salts of the metals M M'M''M''' and of an acid which is easily decomposed by heat. Typical examples of such salts are benzoates, oxalates, carbonates, etc. The precipitate may be formed by the reaction of a water and alcohol solution of heat unstable acids such as benzoic, oxalic, or carbonic acids with an aqueous or alcohol solution of soluble salts of the said metals. Typical examples of such soluble salts are nitrates and acetates. In a specific example, a mixed solution of Thorium, Gallium, Lanthanum and Zirconium salts (Nitrates for instance) is prepared and buffered by the addition of an organic base (diethanolamine for instance) at a temperature not exceeding 80° C. Precipitation may also be obtained by slowly adding solutions in water and alcohol of salts from said acids in which the cations are alkali metals or ammonium. The precipitate is separated by filtration or centrifugation, washed with distilled water, and the wet paste is charged into an autoclave where it is maintained at a controlled temperature not exceeding 180° C. for a week. The resulting mixed crystals are then air dried in an oven at 80° C. and compacted into pellets. These are subsequently incinerated in an autoclave in successively increasing temperature steps. The dissociation of the heat-sensitive crystals into oxides is monitored by following the increase in pressure in the autoclave. At the end of each temperature step, the gaseous products of thermal dissociation are displaced with an inert gas such as steam, or nitrogen. A final step of the heat treatment of the catalyst pellets is their sintering in an inert atmosphere at a temperature not exceeding 1000° C. The resulting mixed oxides pellets may then be used directly in a moving bed reactor or pulverized to a prescribed mesh size for use in a fluid bed reactor. The pulverized catalyst may also be mixed with an organic or inorganic binder, compressed or extruded into pellets and sintered at high temperature according to procedures well known to those skilled in the art.

The structure of the catalyst crystals is that of an irregular cubic system including many dislocations. This is attributed to the fact that below 900° C. pure Zirconia ($ZrO_2$) crystallizes in the monoclinic system whereas pure Thoria ($ThO_2$) crystals are cubic, and Gallium-Lanthanum oxide ($GaLaO_3$) forms orthorombic (perovskite type crystals.

The Rich Gas conversion may be explained by the following successive reactions, overall largely endothermic:

$$C_3H_8 \rightarrow \rightarrow \rightarrow H^* + C_3H_7^* \qquad (1)$$

$$C_3H_7^* + C_3H_8 \rightarrow \rightarrow \rightarrow H_2 + 2C_3H_6^* + H^* \qquad (2)$$

$$2C_3H_6^* \rightarrow \rightarrow \rightarrow C_6H_6 + 3H_2 \qquad (3)$$

in which reaction (1) is rate limiting. Excited states are dotted. The Lean Gas ($C_1C_2$) conversion is initiated through a different reaction, also rate limiting, namely:

$$H_2 \rightarrow \rightarrow \rightarrow 2H^* \qquad (4)$$

This reaction occurs in the plasma derived from a primary hydrogen-rich stream and generated by conventional means (e.g. electromagnetic) within the cyclone reactor. The conversion of $C_1$, $C_2$ is believed to proceed by the following reactions:

$$CH_4 + H^{19} \rightarrow \rightarrow \rightarrow CH_3^* + H_2 \qquad (5)$$

$$CH_3^* + CH_4 \rightarrow \rightarrow \rightarrow C_2H_6^* + H^* \qquad (6)$$

$$C_2H_6^* + H^* \rightarrow \rightarrow \rightarrow C_2H_5^* + H_2 \qquad (7)$$

$$C_2H_5^* + H^{19} \rightarrow \rightarrow \rightarrow C_2H_4 + H_2 \qquad (8)$$

$$3C_2H_4 \rightarrow \rightarrow \rightarrow C_6H_6 + 3H_2 \qquad (9)$$

At high temperature, those reactions (5) to (9) are believed to proceed within the gas phase as well as on the catalyst surface. The dehydrogenation, especially in this gas phase, may continue further until final degradation into carbon and hydrogen, unless exposure of the desirable reaction products ($C_5+$) to the high temperature of the hydrogen plasma remains very short. This is achieved by quenching the intermediate dehydrogenation reactions (5 to 9) with the relatively cold (600° C.) catalyst and by limiting the contact time of the gas phase in the high temperature region of the reactor. Further quenching occurs in the heat recovery section of the reactor.

Cyclone Reactor

FIG. 2 illustrates the concept of the cyclone reactor used to quench the dehydrogenation reactions and to protect the reactor walls (26,28) from thermal radiation emitted by the plasma jet (12). The heat shield (27) made of refractory material protects the top wall (28). The catalyst settling on the cylindro-conical wall (26) and the catalyst in the dispersed phase (30) of the vortex, shield this wall from radiated heat. The primary hydrogen cold stream (11) introduced into the cyclone reactor by means of the insulated pipe (31) is ionized by the high frequency electromagnetic field produced by the water cooled nozzle (25). The secondary hydrogen stream (22) is introduced into the cyclone reactor by means of the insulated pipe (32), and is guided along a spiral path by the guide vanes (33), also shown on cross section on FIG. 3. The catalyst (9) is fed into the cyclone reactor by a standpipe (34) shown on both FIG. 2 and FIG. 3. Elements 15, 16 and 24 are the same as in FIG. 1.

Embodiments of the Invention

A preferred embodiment of the invention is shown on FIG. 4. The cyclone reactor (10) is located within a fluidized bed reactor (5) which is fed by a riser (35) in which the regenerated catalyst (8) is entrained by the Rich Gas feed (2) and recycled Rich Gas (4)

The fluidized bed reactor (5) is similar in concept to that of a FCC reactor. It includes a cyclone (36) which provides the gas phase effluent (6) to the separation unit (7).

Also shown on FIG. 4 is the furnace (14) which preheats the Lean Gas feed prior to injection into the cyclone reactor (10). The gas-solid effluent stream from the cyclone reactor is sent to a disengagement cyclone (17) from which the spent catalyst (19) is fed directly into a steam stripper. The overhead gas effluent (18) from the disengagement cyclone contains all the gaseous reaction products including those stripped from the catalyst, plus unreacted feed and stream. The stripped catalyst (37) is fed by a dipleg (38) directly into the regenerator (39) of conventional design, which includes at least one stage of cyclone (40) to separate the flue gas from the regenerated catalyst (8). A pump (41) or compressor if the Rich Gas feed is in vapor phase, provides the energy for the circulation of the catalyst. The Lean Gas phase fed into the furnace is also recompressed in the separation unit.

Another embodiment of the invention is shown on FIG. 5 in which the catalytic bed reactor (5) is a moving bed reactor of conventional design. The cyclone reactor is located directly below the moving bed reactor. All other elements of the process are the same as in FIG. 4, except that the regenerator (39) is also of the moving bed design, instead of being a fluidized bed regenerator as in FIG. 3. Elements 3, 11, 13, 22 and 23 are the same as described in FIG. 1.

The spent catalyst (37) is collected in a hopper (42) and transfered to a lift pot (43) and from there through a lift line (44) to a feed hopper (45) above the regenerator. Conversely, the regenerated catalyst (8) is collected in a hopper (46) and transferred to a lift pot (47), and from there to a lift line (48) leading to a feed hopper (49) above the moving bed reactor (5). This catalyst transport system, applicable to moving bed catalysts only is familiar to those skilled in the art.

The lift line (48), hopper (46) and lift pot (47) may be omitted in the embodiment of FIG. 5 when the moving bed regenerator (39) is located directly above the moving bed reactor (5) instead of being side by side as shown on FIG. 5.

Still another embodiment of the invention is shown on FIG. 6 in which the stripped catalyst (19) flows by gravity directly from the stripper into the feed hopper (42) of the moving bed regenerator (39). On the flow diagram of FIG. 6, the regenerated catalyst exchanges its sensible heat with the Lean Gas stream in a waste heat recovery exchanger (50) before falling into the hopper (46). It is then lifted to the feed hopper (49) at the top of the moving bed reactor (5) by means of the lift line (48). As in the other two embodiments, the Rich Gas stream is pre-heated in the heat recovery section

(51) of the cyclone reactor (10) prior to being fed to the catalytic bed reactor, in this case a moving bed reactor (5). In a variant of this embodiment, the moving bed regenerator may be located directly above the moving bed reactor (5) and the lift pot (43) and hopper (42) located downstream from the stripper, as in FIG. 5 are used in conjunction with a lift line (44) to feed the spent catalyst to the moving bed regeneration (39). The cooling fluids respectively in the heat recovery exchanger (50) and in the heat recovery section (51) of the cyclone reactor may also be interchanged.

In all previous embodiments the Rich Gas conversion occurs first. In the embodiment shown on FIG. 7, the Lean Gas conversion is obtained with freshly regenerated catalyst and the Rich Gas conversion is achieved in a moving bed reactor using the stripped catalyst resulting from the Lean Gas conversion in the cyclone reactor (10) and subsequent disengagement and stripping of the catalyst. The moving bed regenerator is located at the top, with the catalyst flowing by gravity from the regenerator (39) to the cyclone reactor (10) and from there into the disengagement cyclone (17) and steam stripper from which the stripped catalyst (37) is fed by a standpipe (38) into the moving bed reactor (5) in which conversion of the pre-heated Rich Gas takes place. The spent catalyst is then transferred to the feed hopper (45) of the moving bed regenerator (39) by means of a lift line (44) fed by the lift pot (43) and spent catalyst hopper (42). The lift gas is preferably an inert gas such as Nitrogen. Pre-heating of the Lean Gas stream in the furnace (14) and of the Rich Gas stream in the heat recovery section (51) of the cyclone reactor (10) is obtained as in the previous embodiments. The feed splitter and the separation unit, both of conventional design also have the same functions as before. In another embodiment of the invention shown on FIG. 8 the functions of the cyclone reactor and those of the disengagement cyclone are combined. The Lean Gas stream (3) is fed through an axial inlet (52) at the top and is guided into a rotational path by means of stationary helicoidal blades (53). The heat shield (27) is located immediately below the helicoidal blades (53). It forms an enclosed channel with each blade, through which a secondary hydrogen stream (22) flows from the inlet at the periphery towards the center in a helicoidal path. The swirling hydrogen streams then flow downward in a central vortex around the gas outlet of the cyclone reactor and into the cylindrical cavity around the central plasma jet (12). The secondary cooling hydrogen downward vortices then collide with another secondary hydrogen upward vortex (54) surrounding the plasma jet and rotating in the opposing direction. All the hydrogen gas streams (11) (22) (54) then follow an upward helical path towards the axial gas outlet (55) of the cyclone at the top, together with the gas phase (15) separated from the spent catalyst (19). The spent catalyst (19) flows in a dense phase at the bottom into the heat recovery section (51) of the cyclone reactor, and from there into the catalyst stripper (20). Piping for the primary hydrogen stream and electrical power connections for the generation of the hydrogen plasma pass through the heat recovery section (51) in a hydrogen-cooled insulated pipe (31) along the axis at the lower part of the reactor. The secondary hydrogen cooling stream flows through an annular space concentric with the primary hydrogen pipe (31). An helicoidal guide vane (56) within this annular space imparts to the secondary hydrogen stream a spiraling motion in the direction opposite to that of the Lean Gas stream (3). This disposition of the cyclone reactor shown on FIG. 8 may be substituted for that of FIG. 2 in each of the process diagrams shown on FIGS. 1, 4, 5, 6, and 7. Elements 2, 9, and 24 in FIG. 8, are the same as in FIG. 1, and element 28 is the same as in FIG. 2. When the disposition shown on FIG. 8 is used in the flow diagram of FIG. 7, the catalyst stripper may advantageously be omitted. This is possible because the faster disengagement of the Lean Gas conversion products from the catalyst results in smaller amounts of high molecular weight hydrocarbons saturating the catalyst. It was found however that the Lean Gas conversion yield increased with the presence of light hydrocarbons (ethane to benzene) within the catalyst pores prior to the conversion reaction. This may be obtained in the flow diagram of FIG. 7 by feeding a small amount of Rich Gas in the stand-pipe (34) delivering fresh catalyst into the Cyclone Reactor (10). This optional disposition is not shown on FIG. 7, but may be implemented by those skilled in the art, using conventional techniques.

I claim:

1. An improved process for converting all natural gas hydrocarbon components with carbon numbers of 1 to 4 into liquid hydrocarbons with carbon numbers equal to or greater than 5, and into a hydrogen-rich gaseous by-product; said process comprising the following steps:
   A. Splitting the natural gas feed into a rich gas stream comprising $C_2$, $C_3$ and $C_4$ hydrocarbons and a lean gas stream comprising $C_1$ and $C_2$ hydrocarbons;
   B. Catalytically converting said rich gas stream in a catalytic bed reactor in which the gas-suspended solid phase is a catalyst maintained at a temperature not exceeding 600° C.;
   C. Separating the gaseous effluent from said said catalytic bed reactor into (1) a hydrogen-rich stream, (2) a lean gas stream comprising hydrogen, $C_1$ and $C_2$ hydrocarbons, (3) a rich gas stream comprising $C_2$, $C_3$ and $C_4$ hydrocarbons and (4) a liquid product stream comprising $C_5+$ hydrocarbons;
   D. Pre-heating all lean gas streams, including recycle, in a furnace;
   E. Transferring said catalyst into a short residence time reactor;
   F. Reacting an ionized plasma derived from said hydrogen stream with said pre-heated lean gas stream carrying said transferred catalyst in said short residence time reactor at a temperature ranging from 600° C. to 900° C. and at a residence time ranging from 100 to 300 milliseconds, with subsequent quenching of reactions;
   G. Separating the gas-solid stream resulting from said reaction into a spent catalyst phase stream and a gaseous effluent stream through disengagement by centrifugal forces;
   H. Separating said gaseous effluent stream from said disengagement means into four streams as defined in step C, using the same separation facilities as in step C;
   I. Regenerating said spent catalyst stream in a regenerator by combustion of the carbon build-up on said spent catalyst in an oxidizing gas stream;
   J. Transferring the regenerated catalyst back into said catalytic bed reactor and into said short residence time reactor;
   K. Recycling all rich gas streams obtained in steps C and H back to said catalytic bed reactor;

L. Recycling the lean gas stream obtained in step H back to said pre-heating furnace of step D.

2. A process according to claim 1 wherein said catalyst used in said catalytic bed and short residence time reactors includes a crystalline form of refractory mixed oxides of composition $xMO_2$, $yM'M''O_3$ and $zM'''O_2$ where x, y and z are mole fractions with values comprised between 0 and 98%, and where
M is a Actinide metal,
M' is a Lanthanide metal,
M" is gallium,
M'" is zirconium,
and where x is greater than y and y is greater than z.

3. A process according to claim 2 wherein said crystalline form of refractory mixed oxides is obtained by:
A. Forming a precipitate from a water and alcohol solution of soluble salts of metals MM'M"M'" buffered with an organic base, using as a precipitation reagent a solution in water and alcohol of a heat-decomposable acid or a salt of a heat-decomposable acid;
B. Heating the washed precipitate in an autoclave in the presence of steam;
C. Air drying the resulting crystals;
D. Compacting said air dried crystals into pellets;
E. Heating said pellets in an inert atmosphere exceeding the decomposition temperature of said acid; and
F. Sintering said pellets at 1,000° C. in the presence of steam.

4. A process according to claim 3 wherein said precipitation reagent is a solution in water and alcohol of a salt of a heat-decomposable acid in which the cations are selected from the group consisting of alkali metals and ammonium.

5. A process according to claim 3 wherein:
A. Said heat-decomposable acid is selected from the group consisting of benzoic acid, oxalic acid, carbonic acid and mixtures thereof; and
B. Said organic base used to buffer said solution is selected from the group consisting of pyridine, diethanolamine and propanediamine.

6. A process according to claim 1 wherein the temperature of said catalytic bed reactor does not exceed 600° C. and the residence time exceeds 3 seconds.

7. A process according to claim 1 wherein said lean gas stream is pre-heated to a temperature not exceeding 1,000° C.

8. A catalytic process for converting the light components of natural gas having hydrocarbons of carbon numbers of 1 to 3 into hydrocarbons of carbon number greater than 3 in the presence of atomic hydrogen, for a short residence time, wherein the short residence time reactor is a cyclone reactor characterized by having:
A. In its upper part, a vertical cylindrical cavity equipped with at least:
1. An inlet by which a pre-heated lean gas stream comprising $C_1$ and $C_2$ hydrocarbons is injected and set into rotational flow, and
2. A vertical peripheral inlet from which a catalyst at a temperature not exceeding 600° C. flows into the tangential flow of said pre-heated lean gas;
B. Along its vertical axis, an ionized hydrogen plasma jet stream;
C. A hydrogen-cooled heat shield made of refractory materials, protecting the upper part of said cyclone reactor from the heat radiated by said hydrogen plasma;
D. A plurality of secondary hydrogen cooling streams and means for injecting them into said cylindrical cavity and for setting them into rotational flows, with the direction of at least one rotating hydrogen stream opposite to that of said lean gas stream; and
E. In its lower part, a co-axial conical cavity with a bottom outlet from which spent catalyst flows while exchanging heat with a rich gas stream comprising hydrocarbons of carbon numbers of 2 and 3 in a heat recovery section of the reactor located below said conical cavity.

9. A process according to claim 8 wherein the top surface of said cyclone reactor is conical, with an internal angle from the horizontal at least equal to the angle of repose of said catalyst.

10. A process according to claim 8 wherein the inner top conical surface of said cyclone reactor and the back face of said heat shield are cooled by cold secondary hydrogen streams also injected into said cyclone reactor top at a plurality of points above the pheriphery of said heat shield and guided along spiral trajectories toward a central annular collector from which said secondary hydrogen streams flow first downward through openings in said heat shield and along spiral trajectories around the vertical axis of said plasma stream.

11. A process according to claim 8 wherein the direction of rotation of the trajectories of at least one of said secondary hydrogen streams is opposite to that of the vortex formed by the catalyst and lean gas stream injected into said cyclone reactor so that turbulent mixing occurs.

12. A process according to claim 1 wherein said spent catalyst is regenerated by combustion of the residual carbon on said catalyst with a mixture of oxygen, nitrogen and steam.

13. A process according to claim 12 wherein said catalyst regeneration occurs at temperatures not exceeding 600° C.

14. A process according to claim 8 wherein said cyclone reactor is locaed within the fluidized bed of said catalytic bed reactor so that the heat transferred from the outer wall of said cyclone reactor contributes to maintaining the surrounding fluidized catalyst and rich gas in said catalytic bed reactor at the appropriate temperatures required for the endothermic reactions of conversions to proceed.

15. A process according to claim 12 wherein said regenerated catalyst flows co-currently with an oxygen-free lift gas to a point above the surface of the catalyst bed in said catalytic bed reactor and falls on the top conical surface of said cyclone reactor.

16. A process according to claim 12 wherein said catalyst in said catalytic bed reactor and in said regenerator flows downward by gravity counter-current to the gas phase.

17. A process according to claim 14 wherein:
A. The external angle of the conical cavity of said cyclone reactor from the horizontal exceeds the angle of internal friction of said catalyst pellets;
B. The upper surface of the heat recovery section in said cyclone reactor is conical with an internal angle from the horizontal at least equal to the angle of repose of said catalyst pellets; and
C. The distribution of said rich gas stream into said fluidized bed does not extend within the circle projecting vertically from the upper part of said cyclone reactor.

* * * * *